(12) United States Patent  
Bode

(10) Patent No.: US 9,174,000 B2
(45) Date of Patent: Nov. 3, 2015

(54) DRUG DELIVERY DEVICE WITH BIODEGRADABLE PLASTIC COMPONENTS

(75) Inventor: Andreas Bode, Frankfurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 13/500,794

(22) PCT Filed: Oct. 8, 2010

(86) PCT No.: PCT/EP2010/065094
§ 371 (c)(1),
(2), (4) Date: Oct. 5, 2012

(87) PCT Pub. No.: WO2011/042537
PCT Pub. Date: Apr. 14, 2011

(65) Prior Publication Data
US 2013/0023830 A1 Jan. 24, 2013

(30) Foreign Application Priority Data
Oct. 8, 2009 (EP) .................................... 09172505

(51) Int. Cl.
*A61F 13/15* (2006.01)
*A61M 5/24* (2006.01)
(Continued)

(52) U.S. Cl.
CPC ............ *A61M 5/24* (2013.01); *A61F 13/15252* (2013.01); *A61M 5/3129* (2013.01); *A61M 5/31525* (2013.01); *A61M 5/31533* (2013.01); *A61M 5/3202* (2013.01)

(58) Field of Classification Search
CPC ................ A61M 5/31525; A61M 5/31535; A61M 5/31543; A61M 5/14; A61F 13/2051; A61F 13/15252
USPC .................. 604/358, 187, 181; 528/295.3
See application file for complete search history.

(56) References Cited

U.S. PATENT DOCUMENTS 3,649,341 A * 3/1972 Tammela et al. ............. 427/308
3,939,286 A * 2/1976 Jelks ............................. 426/312
(Continued)

FOREIGN PATENT DOCUMENTS

EP 0327910 8/1989
EP 1498460 1/2005
(Continued)

OTHER PUBLICATIONS

Beguin et al., The biological degradation of cellulose. FEMS Microbiology Reviews. vol. 13, Iss. 1, p. 25. Jan. 1994.*
(Continued)

*Primary Examiner* — Aarti B Berdichevsky
*Assistant Examiner* — Matthew A Engel
(74) *Attorney, Agent, or Firm* — McDonnell Boehnen Hulbert & Berghoff LLP

(57) ABSTRACT

The present invention relates to drug delivery device for dispensing of a predefined amount of a medicinal product, comprising:
  at least one housing component (2),
  a cartridge holder component (4) to receive a product-containing cartridge (3), the cartridge having a piston slidably arranged therein,
  a drive mechanism component operably engageable with the piston of the cartridge (3) for dispensing of a dose of the medicinal product,
wherein at least one of said components (2, 4, 6) at least partially comprises a biodegradable plastic material comprising at least one additive adapted to modify a degradation process of the plastic material.

21 Claims, 1 Drawing Sheet

(51) Int. Cl.
*A61M 5/31* (2006.01)
*A61M 5/315* (2006.01)
*A61M 5/32* (2006.01)

(56) References Cited

U.S. PATENT DOCUMENTS

| | | | | |
|---|---|---|---|---|
| 4,302,252 | A * | 11/1981 | Turbak et al. | 106/200.3 |
| 4,936,833 | A * | 6/1990 | Sams | 604/232 |
| 4,944,734 | A * | 7/1990 | Wallach | 604/358 |
| 5,292,783 | A * | 3/1994 | Buchanan et al. | 524/37 |
| 5,346,929 | A | 9/1994 | Guttag | |
| 5,444,113 | A * | 8/1995 | Sinclair et al. | 524/306 |
| 5,514,097 | A * | 5/1996 | Knauer | 604/136 |
| 5,607,395 | A * | 3/1997 | Ragsdale et al. | 604/130 |
| 5,665,831 | A * | 9/1997 | Neuenschwander et al. | 525/415 |
| 6,160,084 | A * | 12/2000 | Langer et al. | 528/272 |
| 6,186,235 | B1 * | 2/2001 | Tjon-Joe-Pin et al. | 166/300 |
| 6,191,196 | B1 * | 2/2001 | Willett et al. | 524/13 |
| 6,211,358 | B1 * | 4/2001 | Honda et al. | 536/64 |
| 6,322,797 | B1 * | 11/2001 | Mao et al. | 424/78.37 |
| 6,440,106 | B1 * | 8/2002 | Yoon | 604/218 |
| 6,478,780 | B1 * | 11/2002 | Shields | 604/263 |
| 6,669,771 | B2 * | 12/2003 | Tokiwa et al. | 106/162.7 |
| 8,142,806 | B2 * | 3/2012 | Gupta et al. | 424/422 |
| 8,143,368 | B2 * | 3/2012 | Domb et al. | 528/295.3 |
| 8,251,951 | B2 | 8/2012 | Suzuki | |
| 2001/0028955 | A1 * | 10/2001 | Luo et al. | 428/393 |
| 2002/0183696 | A1 * | 12/2002 | Yoon | 604/187 |
| 2005/0070874 | A1 * | 3/2005 | Matsuda et al. | 604/500 |
| 2006/0018941 | A1 * | 1/2006 | Matsuda et al. | 424/422 |
| 2008/0223245 | A1 * | 9/2008 | Stevens et al. | 102/453 |
| 2010/0042047 | A1 * | 2/2010 | Suzuki | 604/110 |
| 2010/0172889 | A1 * | 7/2010 | Catchmark et al. | 424/94.1 |
| 2011/0033906 | A1 * | 2/2011 | Jo et al. | 435/161 |
| 2011/0270197 | A1 * | 11/2011 | Weill et al. | 604/187 |
| 2012/0022460 | A1 * | 1/2012 | Horvath et al. | 604/192 |
| 2012/0315688 | A1 * | 12/2012 | Patel | 435/262.5 |

FOREIGN PATENT DOCUMENTS

| | | |
|---|---|---|
| EP | 1938854 | 7/2008 |
| GB | 1366207 | 9/1974 |
| JP | 2003-522823 | 7/2003 |
| JP | 2004-075727 | 3/2004 |
| JP | 2007-185499 | 7/2007 |
| WO | 01/60437 | 8/2001 |
| WO | 2007/028731 | 3/2007 |
| WO | 2008/038350 | 4/2008 |

OTHER PUBLICATIONS

Form PCT/IB/326, Notification Concerning Transmittal of International Preliminary Report on Patentability.
European Search Report for European App. No. 09172505, completed Mar. 26, 2010.
International Search Report for International App. No. PCT/EP2010/065094, completed Feb. 3, 2011.

* cited by examiner

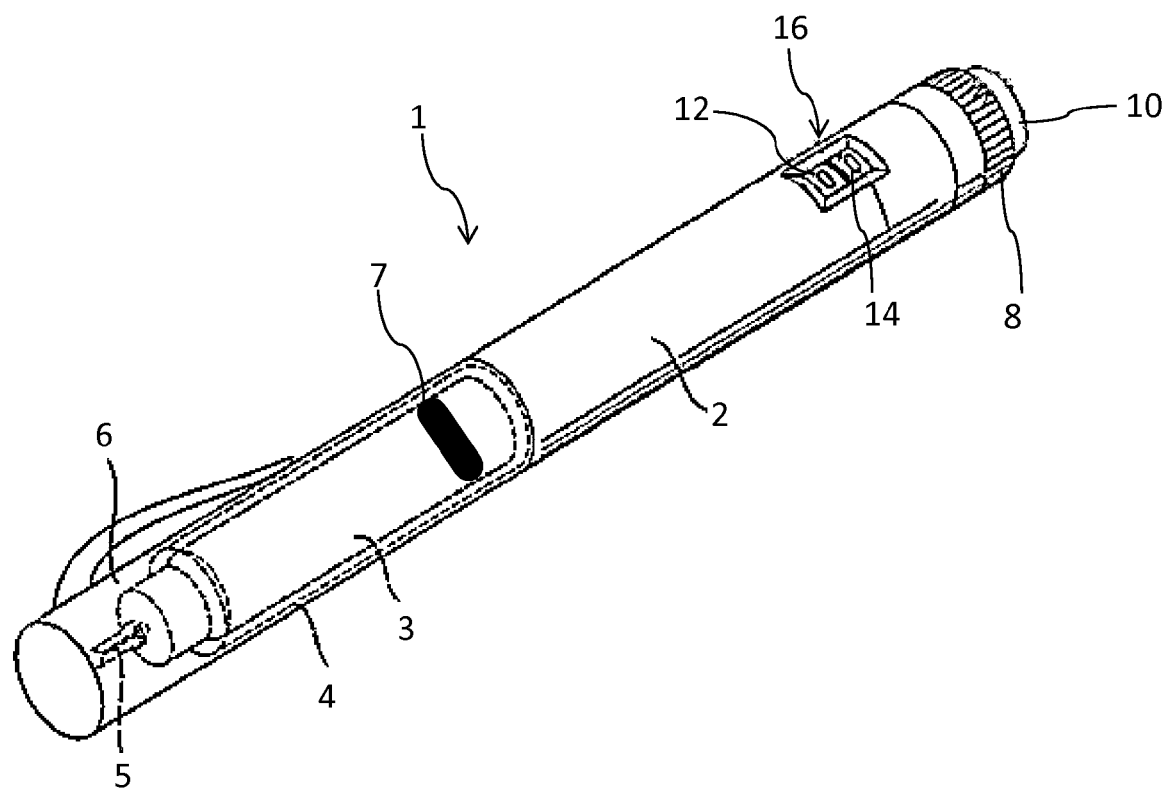

DRUG DELIVERY DEVICE WITH BIODEGRADABLE PLASTIC COMPONENTS

CROSS REFERENCE TO RELATED APPLICATIONS

The present application is a U.S. National Phase Application pursuant to 35 U.S.C. §371 of International Application No. PCT/EP2010/065094 filed Oct. 8, 2010, which claims priority to European Patent Application No. 09172505.1 filed on Oct. 8, 2009. The entire disclosure contents of these applications are herewith incorporated by reference into the present application.

FIELD OF THE INVENTION

The present invention relates to a drug delivery device that allows a user to select multiple doses of an injectable medicinal product and for the dispensing of the set dosage and applying said product to a patient, preferably by injection. In particular, the invention relates to such devices, which are handled by the users or patients themselves.

BACKGROUND AND PRIOR ART

Drug delivery devices, which allow multiple dosing of the required dosage of liquid drug and administration of the liquid to a patient, are well known in the art. Generally, such devices have substantially the same purpose as that of an ordinary syringe.

Injectors of this kind must meet a number of requirements to match a user's needs. The devices have to be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be cheap to manufacture and easy to dispose of. Preferably, the drug delivery device should be suitable for recycling.

Typical drug delivery devices, e.g. pen-type injectors comprise numerous components, such as a housing, a cartridge holder and a drive mechanism, wherein the drive mechanism is adapted to apply thrust on a piston of a cartridge containing the medicinal product or drug to be dispensed in doses by the device. At least some of the components of such drug delivery devices, in particular a removable cap, a housing and/or a cartridge holder are manufactured as injection moulded plastic parts that are generally demanded to fulfil requirements regarding mechanical stability and rigidity and yet generally have to comply with low cost demands regarding the manufacture of such devices.

Usage of user- or patient-operated injection pens and drug delivery devices is growing in number due to a manifold of diseases requiring injection of a respective medicinal product or liquid drug. Among these, diabetes requiring hypodermic or subcutaneous administering of a liquid drug like insulin, plays a predominant role.

Disposable or single-use drug delivery devices typically turn to plastic disposal after use and therefore constitute a burden on the environment, in particular if disposed in landfills.

OBJECT OF THE INVENTION

It is therefore an object of the present invention, to provide a drug delivery device for dispensing of a medicinal product, which reduces the burden on the environment and which provides an increased environmental compatibility. Also, the drug delivery device should be inexpensive to produce as well as fast and easy to assemble. Furthermore, the drug delivery device and its numerous components should be mechanically stable and robust.

SUMMARY OF THE INVENTION

The drug delivery device according to the present invention is adapted for dispensing of a medicinal product in a well-defined way, in particular of a liquid drug, like heparin or insulin. The device is particularly adapted to dispense pre-defined amounts of the medicinal product by setting and subsequently dispensing of a predefined dose of the medicinal product. The drug delivery device comprises at least one housing component, which is particularly adapted to house a drive mechanism and respective drive mechanism components, wherein at least one of the drive mechanism components is operably engageable with a piston of a cartridge containing the medicinal product to be dispensed.

The drug delivery device further comprises a cartridge holder component, which is adapted to receive and to hold the product-containing cartridge. The cartridge, typically of substantially cylindrical shape, comprises a piston being displaceably arranged therein. Under the impact of distally applied thrust, the piston moves in distal direction, thereby expelling a predefined dose of the liquid medicinal product from the cartridge.

A distal outlet of the cartridge can be coupled with a needle, a cannula, an infusion tube or with similar delivery devices in a fluid-transferring way. The cartridge itself can be designed as replaceable or disposable ampoule, carpoule, syringe or as a similar, medicinal product-containing container.

For the purpose of applying thrust to the cartridge's piston, the drive mechanism may comprise a piston rod, a lead screw or a drive sleeve adapted to abut the proximal end face of the piston either directly or by means of interposition of a pressure piece.

In order to enhance the environmental compatibility of the drug delivery device, at least one of said components of the drug delivery device at least partially comprises a biodegradable plastic material. Generally, not only a single but several components of the drug delivery device, such as housing components, cartridge holder component or at least one component of the drive mechanism can comprise a biodegradable plastic material, adapted for a rather rapid degradation compared to conventional petro-chemical plastic materials and components. In this way, also drug delivery devices, such as injection pens can contribute to an environmentally friendly waste disposal.

In the scope of the present invention, a biodegradable plastic material degrades faster, preferably much faster than conventional petroleum-based plastic materials. The materials to be used with the drug delivery device of the present invention do not necessarily have to match national or international standards, such like ISO EN 13432, that define how quickly and to what extent a plastic must be degraded under commercial composting conditions for it to be called biodegradable. According to the ISO EN 13432 standard, a material is classified as being entirely biodegradable, if 90% of its organic carbon degrades within a maximum of 180 days.

Therefore, the "biodegradable plastic material" according to the present invention does not necessarily have to be biodegraded to a large extent within 90 days in a commercial composting unit. The components of the drug delivery device comprising biodegradable plastic material may biodegrade also on a larger time scale. Preferably, the materials to be used with the at least one component of a drug delivery device feature a biodegradation rate of at least 60%, 50% or 40% within 180 days, 360 days or 720 days under commercial composting conditions.

However, the biodegradable plastic material to be used with the drug delivery device preferably fulfils biodegradability standards as e.g. defined in ISO EN 13432 or in ASTM 6400 US-standard.

Preferably, the biodegradable plastic material comprises at least one additive adapted to modify and/or to control a degradation process of the plastic material. Hence, the plastic material may comprise a base or carrier material being substantially non-biodegradable. It is then due to the additive, to induce and/or to trigger a process in which the base or carrier material substantially degrades.

In a first preferred embodiment, the at least one component of the drug delivery device comprises an organic plastic material, which is derivable from at least one biomass source. Hence, the biodegradable plastic material comprises organic material, which typically degrades aerobically with oxygen or an-aerobically, without oxygen. Also, such organic plastic material might become subject to biomineralisation, in which the organic material is converted into minerals. The organic plastic material or bioplastics to be used for at least one component of the drug delivery device can be derived from renewable biomass sources, such as vegetable oil, corn-, pea- or soy starch. Moreover, said organic plastic material may also be derived from microbiota, wherein biopolymers are accumulated in active sludge biomass.

In a further preferred embodiment, the at least one biodegradable component of the drug delivery device comprises starch- or corn- or soy-based plastic, Polylactic acid plastic (PLA), Poly-3-hydroxybutyrate (PHB), Polyhydroxylkanoate (PHA), Polycaprolactone (PCL), Polyvinyl alcohol (PVA) and/or genetically modified bioplastic material.

By means of a treatment with appropriate acid, the starch component is typically transformed into lactose. By way of polycondensation Polylactic Acid is generated which in its physical properties is comparable to Polyethylene (PE). Such materials feature a neutral Carbon balance during the entire production cycle. Hence, the amount of Carbon bound during plant growth substantially equals the amount of Carbon being released during a degradation process.

By making use of additives, such as glycerine or sorbitol, acting as plasticiser or flexibiliser, also a starch based plastic material can be processed thermo-plastically. By selectively varying the amount of additives, the characteristics of the material can be tailored to the drug delivery device specific requirements.

A Polylactic acid (PLA) can be produced from cane sugar or glucose. It does not only resemble conventional petrochemical mass plastics like Polyethylene (PE) or Polypropylen (PP) in its characteristics and properties. It can also be processed easily on standard manufacturing equipment already used for the production of conventional PE- or PP-based plastic material.

Poly-3-hydroxybutyrate (PHB) is a polyester produced by certain bacteria processing glucose or starch. It also comprises similar properties and characteristics compared to petroplastic Polypropylen. It is entirely biodegradable without residual.

Also Polycaprolactone (PCL) and Polyvinyl alcohol (PVA) belong to the group of polymers with which starch in natural or modified form is commonly used.

Moreover, also fully-synthetic biopolymers, such as Poly-ε-caprolacton can be generally used for the at least one biodegradable component. Also synthetic co-polyester may be suitable for manufacture of the at least one device component. Co-polyester comprise semi-crystalline polymers having such thermal and mechanical properties that are comparable to those of LD-PE.

Additionally, various compounds are conceivable that constitute degradable polymers of a natural and synthetic basis. In particular, the use of bioplastic material comprising a biodegradable synthetic thermoplastic matrix and up to 90% of starch is considered to be beneficial for the present invention. Due to the relative large percentage of starch, the compound material features sufficiently large fat- and oxygen barriers.

In the present context, the term "Genetically modified bioplastic material" refers to plastic material being derived from genetically modified natural sources, like genetically modified corn, soy or wheat. Here, the genetic modification may focus on the biodegradability of the derived bioplastic material.

According to a further preferred embodiment of the invention, at least one component of the drug delivery device, thus, the respective biodegradable plastic material comprises at least one polymer and an additive, wherein the additive is adapted to enforce, to boost or to trigger the degradation process of the at least one polymer or biodegradable plastic compound. The polymer or monomer can be of petro-chemical type. It is rendered biodegradable by the particular additive. Said additives may for instance comprise organic compounds adapted to attract microorganisms when placed into a microbial environment. Hence, the additive acts as a degradation initiator to the plastic, thereby achieving a controlled disintegration process of the polymer into $CO_2$, and $H_2O$ and optionally into other residues.

In an alternative, it is conceivable, that the additive acts as inhibitor for a degradation process. In this way also such plastic materials innately showing substantive degradation behaviour can be used for a component of a drug delivery device. By varying the amount or concentration of the additive, the degradation behaviour of said component can be selectively controlled.

In a further preferred embodiment, the at least one biodegradable component comprises Polyethene (PE), Polypropylene (PP), Polystryrene (PS), Polyethylene terephthalate (PET), Polyvinyl chloride (PVC) and/or copolymers thereof. Any one of these biodegradable plastic materials may comprise conventional petro-chemically-based polymers and at least one additive rendering the respective plastic material biodegradable. Usage of modified petro-chemically-based plastic materials comes along with the advantage, that manufacturing, usage, general handling as well as the mechanical properties of such biodegradable plastic materials are comparable to conventional purely-petro-chemically-based plastics.

Advantageously, a degradation process does not start before the entire drug delivery device or its particular biodegradable plastic component is exposed to a degradable environment. Such behaviour is beneficial, because usage and function of the drug delivery device is then substantially not affected by the biodegradation properties of its components. In this way, an unlimited shelf life of the respective bioplastic component is achievable.

In a further preferred embodiment of the invention, the additive of the polymer-based biodegradable plastic component is sensitive to electromagnetic radiation and/or to heat and/or to moisture and/or to a microbial environment. Depending on the type of additive, the petro-chemically-based plastic material may disintegrate when exposed to electromagnetic radiation, in particular to UV-radiation. Also, heat exposure may trigger or at least boost and enhance a respective degradation process.

The biodegradation of the at least one plastic component of the drug delivery device will further be enhanced and the plastic component will become sensitive to a microbial environment, if the additive placed in the polymer organic compounds is adapted to attract microorganisms when placed in a microbial environment. Attracted microorganisms may produce extra cellular substances, which in turn may initialize, enhance and/or boost the biodegradation process of the plastic component.

According to a further preferred embodiment of the invention, the additive comprises at least one kind of metal ion and a catalyst for splitting of the molecular chains of the polymer in response to an exposure to electromagnetic radiation and/or in response to heat exposure and/or in response to moisture and/or in response to a displacement in a microbial environment.

In particular embodiments, the biodegradable plastic component of the drug delivery device is exclusively sensitive to microorganisms and a respective microbial environment, but remains stable when exposed to electromagnetic radiation and/or to heat or to moisture. In this way, an unlimited shelf life of the respective bioplastic component can be provided and a degradation process is inhibited as long as the device is in use.

In a further preferred embodiment, the at least one biodegradable component of the drug delivery device is manufactured by means of a one- or more-component injection moulding process. Preferably, the biodegradable plastic material of choice is suitable for injection moulding, preferably by means of the same equipment as is used for conventional, purely petro-chemically based plastic materials.

According to a further preferred embodiment of the invention, at least one housing component of the drug delivery device being adapted to house at least parts of the drive mechanism is at least partially, preferably entirely made of biodegradable plastic material. Additionally or alternatively, the cartridge holder and/or a removable needle protection cap is made of one of the above-described and above-specified biodegradable plastic materials.

In particular, the removable needle protection cap can be made of biodegradable plastic material. For instance, it can be easily removed from the drug delivery device after use and can be disposed separately together with other biodegradable waste.

Since the protection cap merely serves to protect the needle being arranged at the distal outlet portion of the drug delivery device and since the cap is not operably engaged with a drive mechanism, almost any biodegradable plastic material being even inferior to conventional petro-chemically-based plastics with respect to mechanical stability and rigidity can be used for said needle cap.

In a further independent aspect, the invention also refers to a usage of at least one biodegradable plastic material in or with a component of a drug delivery device, such as a cartridge holder component, at least one drive mechanism component or a housing component, in particular a removable cap.

Furthermore, and according to another preferred embodiment, the drug delivery device comprises a cartridge filled with the medicinal product. The device may be of reusable and/or disposable type. Preferably, the device is to be commercially distributed with a filled cartridge readily disposed therein and is of disposable type. In this way, after consumption of the medicinal product, the entire device can be discarded and/or supplied to a recycling process. Furthermore, in the process of discarding of a used drug delivery device, biodegradable and non-biodegradable components of the device can be separated and can thus be separately treated as bio-compatible litter and/or as reusable recycling material.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)$_5$-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art, that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

Without any limitation, the present invention will be explained in connection with an example of a particular drug delivery device by making reference to:

FIG. 1 schematically illustrating a drug delivery device and some of its components in a perspective view.

The drug delivery device 1 as depicted in FIG. 1 comprises a pen-type injector. It is particularly applicable for self-administering a dose of a medicinal product. The drug delivery device 1 comprises a housing 2 and a removable cap 6. At its distal end, the device comprises an injection needle 5, which can for instance be removably connected to a distal outlet of the drug delivery device 1. The housing 2 serves to receive a not further illustrated drive mechanism, which is adapted to operably engage with a piston 7 of a cartridge 3 to be disposed and mounted in a cartridge holder 4 of the drug delivery device 1. The drive mechanism typically comprises numerous mechanically interacting components adapted to apply distally directed thrust to the piston 7 of the cartridge 3. In this way, a well-defined dose of the fluid medicinal product can be expelled from the cartridge 3.

At its proximal end section, the drug delivery device 1 comprises a rotating knob 8 and a release knob 10 that allow for setting and dispensing of a dose to be administered. Furthermore, the housing 2 comprises a display window 14, in which an indicator 16 is visible. In the illustrated embodiment, the indicator 16 comprises at least one dose setting dial 12 indicating the amount of medicinal product to be dispensed by the drug delivery device 1.

At least one of the illustrated components of the drug delivery device 1 or even the entire drug delivery device 1 at least partially comprises a biodegradable plastic material.

Preferably, at least the removable cap 6 is made of at least one of the above-described biodegradable plastic materials. Depending on the characteristics and mechanical properties of the biodegradable plastic material of choice, also the housing 2, the rotating knob 8, the release knob 10, the indicator unit 16 and/or the cartridge holder 4 may be manufactured as biodegradable plastic components. In this way, the environmental compatibility of the drug delivery device 1 or at least of some of its components can be enhanced.

It is further to be noted, that the illustrated embodiment according to FIG. 1 only exemplary illustrates a typical pen-type injector. Design and functionality of the drive mechanism and the indicator unit 16 as well as the arrangement of release knob 10 or rotating knob 8 may vary arbitrarily. Actuation means, such as rotating knob 8 or release knob 10 may be for instance designed in a completely different way. Dose setting and/or dose dispensing may for instance be controlled by means of translational displaceable actuation means.

LIST OF REFERENCE NUMERALS 1 device
2 housing
3 cartridge
4 cartridge holder
5 needle
6 removable cap
8 rotating knob
10 release knob
12 dose setting dial
14 display window

The invention claimed is:

1. A user operated pen-type injector for dispensing a user settable amount of a medicinal product, comprising:
   a cartridge holder configured to receive and hold a product-containing cartridge,
   the cartridge mountable in the cartridge holder and comprising a piston slidably arranged therein,
   at least one housing component operably coupled to the cartridge holder,
   a drive mechanism component operably engageable with the piston of the cartridge for dispensing a user settable dose of the medicinal product,
   wherein at least one of the cartridge holder, the cartridge, the at least one housing component, and the drive mechanism at least partially comprises a plastic material comprising a substantially non-biodegradable polymer as a base material and at least one additive, the at least one additive adapted to induce or to trigger a degradation process of the base material,
   wherein the at least one additive comprises at least one kind of metal ions and a catalyst for splitting of molecular chains of the substantially non-biodegradable polymer in response to an exposure to at least one of electromagnetic radiation, heat, moisture, and a microbial environment,
   wherein the at least one additive renders at least one of the cartridge holder, the cartridge, the at least one housing component, and the drive mechanism biodegradable thereby forming an at least one biodegradable component, and
   wherein the degradation process does not start until the at least one biodegradable component is exposed to at least one of electromagnetic radiation, heat, moisture, and the microbial environment.

2. The pen-type injector of claim 1 further comprising a rotating knob configured to allow the user to set the user settable amount of the medicinal product.

3. The pen-type injector of claim 2 further comprising a release knob configured to allow the user to dispense the user settable amount of the medicinal product.

4. The pen-type injector according to claim 1, wherein the at least one biodegradable component comprises an organic plastic material, derivable from at least one biomass source.

5. The pen-type injector according to claim 1, wherein the at least one biodegradable component comprises Starch- or Corn-based plastic, Polylactic acid plastic (PLA), Poly-3-hydroxybutyrate (PHB), Polyhydroxyalkanoate (PHA), Polycaprolactone (PCL), Polyvinyl alcohol (PVA) and/or Genetically modified bioplastic material.

6. The pen-type injector according to claim 1, wherein the at least one biodegradable component comprises Polyethene (PE), Polypropylene (PP), Polystyrene (PS), Polyethylene terephthalate (PET), Polyvinyl chloride (PVC) or copolymers thereof.

7. The pen-type injector according to claim 1, wherein the at least one additive is sensitive to the electromagnetic radiation, heat, moisture, or microbial environment.

8. The pen-type injector according to claim 1, wherein the at least one component is manufactured by means of a one- or more-component injection molding.

9. The pen-type injector according to claim 1, wherein the housing component and/or the cartridge holder and/or a needle protection cap entirely comprise a biodegradable plastic material.

10. The pen-type injector according to claim 1, wherein the cartridge is filled with the medicinal product.

11. The pen-type injector of claim 1 wherein said pen-type injector comprises a single use pen-type injector.

12. A user operated pen-type injector for dispensing a user settable amount of a medicinal product, comprising:
   a cartridge holder configured to receive and hold a product-containing cartridge,
   the cartridge mountable in the cartridge holder and comprising a piston slidably arranged therein,
   at least one housing component operably coupled to the cartridge holder,
   a drive mechanism component operably engageable with the piston of the cartridge for dispensing a user settable dose of the medicinal product,
   wherein at least one of the cartridge holder, the cartridge, the at least one housing component, and the drive mechanism at least partially comprises a plastic material comprising a substantially non-biodegradable polymer as a carrier material and at least one additive, the at least one additive adapted to induce or to trigger a degradation process of the carrier material,
   wherein the at least one additive comprises at least one kind of metal ions and a catalyst for splitting of molecular chains of the substantially non-biodegradable polymer in response to an exposure to at least one of electromagnetic radiation, heat, moisture, and a microbial environment,
   wherein the at least one additive renders at least one of the cartridge holder, the cartridge, the at least one housing component, and the drive mechanism biodegradable thereby forming an at least one biodegradable component, and wherein the degradation process does not start until the at least one biodegradable component is exposed to at least one of electromagnetic radiation, heat, moisture, and the microbial environment.

13. The pen-type injector of claim 12 further comprising a rotating knob configured to allow the user to set the user settable amount of the medicinal product.

14. The pen-type injector of claim 13 further comprising a release knob configured to allow the user to dispense the user settable amount of the medicinal product.

15. The pen-type injector according to claim 12, wherein the at least one biodegradable component comprises an organic plastic material, derivable from at least one biomass source.

16. The pen-type injector according to claim 12, wherein the at least one biodegradable component comprises Starch- or Corn-based plastic, Polylactic acid plastic (PLA), Poly-3-hydroxybutyrate (PHB), Polyhydroxyalkanoate (PHA), Polycaprolactone (PCL), Polyvinyl alcohol (PVA) and/or Genetically modified bioplastic material.

17. The pen-type injector according to claim 12, wherein the at least one biodegradable component comprises Polyethene (PE), Polypropylene (PP), Polystyrene (PS), Polyethylene terephthalate (PET), Polyvinyl chloride (PVC) or copolymers thereof.

18. The pen-type injector according to claim 12, wherein the at least one additive is sensitive to the electromagnetic radiation, heat, moisture, or a microbial environment.

19. The pen-type injector according to claim 12, wherein the housing component and/or the cartridge holder and/or a needle protection cap entirely comprise a biodegradable plastic material.

20. The pen-type injector according to claim 12, wherein the cartridge is filled with the medicinal product.

21. The pen-type injector of claim 12 wherein said pen-type injector comprises a single use pen-type injector.

* * * * *